US010251969B2

(12) United States Patent
Prax

(10) Patent No.: US 10,251,969 B2
(45) Date of Patent: Apr. 9, 2019

(54) HVAC FLUID DISPERSANT SYSTEM

(71) Applicant: Xavier Rex Prax, Willoughby Hills, OH (US)

(72) Inventor: Xavier Rex Prax, Willoughby Hills, OH (US)

( * ) Notice: Subject to any disclaimer, the term of this patent is extended or adjusted under 35 U.S.C. 154(b) by 217 days.

(21) Appl. No.: 15/213,226

(22) Filed: Jul. 18, 2016

(65) Prior Publication Data
US 2017/0128611 A1 May 11, 2017

Related U.S. Application Data

(60) Provisional application No. 62/193,377, filed on Jul. 16, 2015.

(51) Int. Cl.
| A61L 9/00 | (2006.01) |
| F24F 7/007 | (2006.01) |
| A61L 9/14 | (2006.01) |
| A61K 9/00 | (2006.01) |
| F24F 3/16 | (2006.01) |
| F24F 13/02 | (2006.01) |

(52) U.S. Cl.
CPC ............... *A61L 9/14* (2013.01); *A61K 9/007* (2013.01); *F24F 3/16* (2013.01); *F24F 13/02* (2013.01); *A61L 2209/134* (2013.01); *A61L 2209/14* (2013.01); *A61L 2209/16* (2013.01); *F24F 2003/1675* (2013.01); *F24F 2003/1689* (2013.01); *F24F 2221/225* (2013.01)

(58) Field of Classification Search
CPC .......... B01D 46/0002; B01D 2265/023; F16G 11/00; A61L 9/14
USPC ........... 422/1, 305–306; 134/22.11; 454/228, 454/237
See application file for complete search history.

(56) References Cited

U.S. PATENT DOCUMENTS

| 2002/0100517 A1* | 8/2002 | Somerville ........... F16L 59/025 138/148 |
| 2005/0269254 A1* | 12/2005 | Roitman .............. B01D 5/0072 210/252 |
| 2012/0280059 A1* | 11/2012 | Jan ...................... B01F 15/0479 239/142 |

FOREIGN PATENT DOCUMENTS

WO  WO 93/22603  * 11/1993  ............... F24F 3/16

* cited by examiner

*Primary Examiner* — Monzer R Chorbaji
(74) *Attorney, Agent, or Firm* — Dodd Call Black, PLLC; Dustin Call

(57) ABSTRACT

An HVAC fluid dispersant system. The HVAC fluid dispersant system includes one or more fluid lines, the one or more fluid lines configured to allow movement of a fluid and a pump, the pump configured to move the fluid through the one or more fluid lines. The HVAC fluid dispersant system also includes a source line, the source line configured to provide the fluid to the pump and a nozzle. The nozzle is configured to receive the fluid from the one or more fluid lines, create a mist composed of the fluid and attach to a duct vent.

18 Claims, 9 Drawing Sheets

HVAC FLUID DISPERSANT SYSTEM

CROSS-REFERENCE TO RELATED APPLICATIONS

This application claims the benefit of and priority to U.S. Provisional Patent Application Ser. No. 62/193,377 filed on Jul. 16, 2015, which application is incorporated herein by reference in its entirety.

BACKGROUND OF THE INVENTION

In many cases the interior walls of the HVAC ductwork is lined and coated with layers of unwanted particulate matter. According to many independent studies and reports, sick building syndrome (SBS) is related to employee absenteeism, medical costs, reduced productivity, and lower earnings. This build-up of sediments is hazardous to the occupants' health. The harmful residue is created from pollen, dead skin cells, dust, dander, smoke, toilet spray mist droplets, and other matters. Another common contributing factor for poor indoor air quality (IAQ) includes the presence of mold and other undetected airborne contaminants which can grow and proliferate within the ductwork system. This common germ infested environment is commonly found in commercial buildings, hospitals, cruise ships, hotels and residential indoor air systems. A review panel comprising medical and engineering experts in the fields of microbiology, medicine, epidemiology, indoor air quality, building ventilation, etc.

Current HVAC humidity and fragrant systems in the market, generate pump and use the HVAC forced air transport humidity moisture and/or room air fragrance which then travel throughout the contaminated duct system. This action allows for the humidity and/or scented fragrance to come in direct contact and interact with these unhealthy airborne contaminants. Furthermore in other open air misting systems, there is a use of aerosol gases which disperse various germ, odor or room freshener sprays. Furthermore this system can dispense, distribute and mist botanical plant based essential oils formula versus the use of chemically derived sprays, which are designed to combat mold, germs, odors and bacteria.

Accordingly, there is a need in the art for a system that works throughout the duct system with a non-contact and non-aerosol fashion and offers a healthier indoor respiratory option. Further, there is a need for the system to allow for a post air supply vent misting a fluid line may also be directly routed to delivery antimicrobial solutions misting onto the HVAC unit filters. Furthermore, there is a need for the system to allow, in the event that multiple fluids are required such as water for humidity and an antibacterial and/or antimicrobial solution, two separate single fluid lines and two separate single misting nozzles. This prevents the pure filtered water for humidification and or other formulas from becoming contaminated. In addition, there is a need for the system to be applied to various types of commercial, residential, health care facilities, cruise ships, yachts and aircrafts HVAC systems. Finally, there is a need for the installation of the system to be minimally intrusive and may be positioned within pre-existing and new HVAC duct systems.

BRIEF SUMMARY OF SOME EXAMPLE EMBODIMENTS

This Summary is provided to introduce a selection of concepts in a simplified form that are further described below in the Detailed Description. This Summary is not intended to identify key features or essential characteristics of the claimed subject matter, nor is it intended to be used as an aid in determining the scope of the claimed subject matter.

One example embodiment includes an HVAC fluid dispersant system. The HVAC fluid dispersant system includes one or more fluid lines, the one or more fluid lines configured to allow movement of a fluid and a pump, the pump configured to move the fluid through the one or more fluid lines. The HVAC fluid dispersant system also includes a source line, the source line configured to provide the fluid to the pump and a nozzle. The nozzle is configured to receive the fluid from the one or more fluid lines, create a mist composed of the fluid and attach to a duct vent.

Another example embodiment includes an HVAC fluid dispersant system. The HVAC fluid dispersant system includes one or more fluid lines, the one or more fluid lines configured to allow movement of a fluid and fluid line insulation. The HVAC fluid dispersant system moreover includes a pump, the pump configured to move the fluid through the one or more fluid lines. The HVAC fluid dispersant system also includes a source line, the source line configured to provide the fluid to the pump and a nozzle. The nozzle is configured to receive the fluid from the one or more fluid lines, create a mist composed of the fluid and attach to a duct vent. The HVAC fluid dispersant system further includes a control system wherein the control system is configured to control operation of the system based on a set of conditions.

Another example embodiment includes an HVAC fluid dispersant system. The HVAC fluid dispersant system includes one or more fluid lines, the one or more fluid lines carrying a fluid and fluid line insulation. The HVAC fluid dispersant system moreover includes a pump, the pump moving the fluid through the one or more fluid lines. The HVAC fluid dispersant system also includes a source line, the source line providing the fluid to the pump. The nozzle receives the fluid from the one or more fluid lines, creates a mist composed of the fluid and attaches to a duct vent. The nozzle includes an aperture, the aperture allowing the mist to exit the nozzle. The HVAC fluid dispersant system further includes a rear anchor, the rear anchor preventing the nozzle from extending beyond the duct vent more than a predetermined amount. The HVAC fluid dispersant system additionally includes a fastening band, the fastening band securing the rear anchor to the nozzle. The HVAC fluid dispersant system moreover includes a front collar the front collar preventing the nozzle from retracting into the duct vent more than a predetermined amount. The HVAC fluid dispersant system also includes a control system wherein the control system controls operation of the system based on a set of conditions.

These and other objects and features of the present invention will become more fully apparent from the following description and appended claims, or may be learned by the practice of the invention as set forth hereinafter.

BRIEF DESCRIPTION OF THE DRAWINGS

To further clarify various aspects of some example embodiments of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION OF SOME EXAMPLE EMBODIMENTS

Reference will now be made to the figures wherein like structures will be provided with like reference designations. It is understood that the figures are diagrammatic and schematic representations of some embodiments of the invention, and are not limiting of the present invention, nor are they necessarily drawn to scale.

Figure 1:
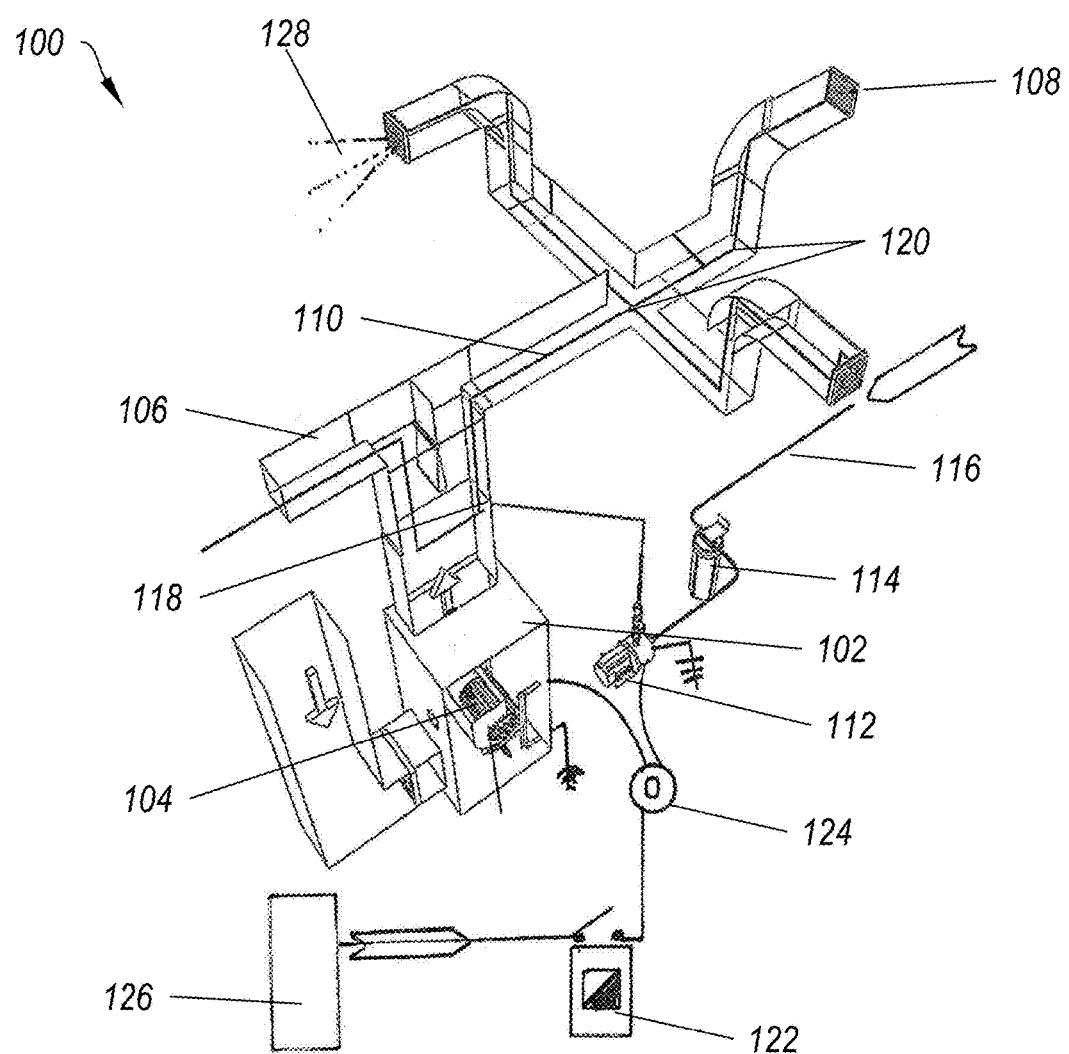
FIG. 1 illustrates an example of a HVAC fluid dispersant system.

FIG. 1 illustrates an example of a HVAC (heating, ventilating, and air conditioning) fluid dispersant system 100. The HVAC fluid dispersant system 100 can be used to add an indoor room humidifier or other features to a new or existing HVAC system. E.g., the HVAC fluid dispersant system 100 can allow a humidifying system to an existing HVAC system without having to remove or replace the HVAC system. The HVAC fluid dispersant system 100 works independently of, but can be coordinated with, the HVAC system itself. Likewise, the HVAC fluid dispersant system 100 can be used to dispense other fluids, such as antimicrobial solutions, air freshening (fragrance) fluids, aromatherapy fluids or any other desired fluids.

FIG. 1 shows that the HVAC fluid dispersant system 100 can include an air handler 102. An air handler, or air handling unit (often abbreviated to AHU), is a device used to regulate and circulate air as part of a HVAC system. An air handler is usually a large metal box containing a blower, heating or cooling elements, filter racks or chambers, sound attenuators, and dampers although some of these elements may be missing.

FIG. 1 also shows that the HVAC fluid dispersant system 100 can include a blower 104. The blower may operate at a single speed, offer a variety of set speeds, or be driven by a variable frequency drive to allow a wide range of air flow rates. Flow rate may also be controlled by inlet vanes or outlet dampers on the fan. Multiple blowers may be present in large commercial air handling units, typically placed at the end of the air handler 102 and the beginning of the supply ductwork (therefore also called "supply fans"). They are often augmented by fans in the return air duct ("return fans") pushing the air into the air handler 102.

FIG. 1 further shows that the HVAC fluid dispersant system 100 can include a duct system 106 (or "ductwork"). Duct systems 106 are used to deliver and remove air. The duct system 106 is connected to the air handler 102 to allow air pushed by the blower 104 to move throughout the space serviced by the HVAC system FIG. 1 also shows that the HVAC fluid dispersant system 100 can include a duct vent 108. The duct vent 108 allows air moved by the blower 104 to exit the duct system 106. For example, the duct vent 108 can be placed in a room that is to receive treated air. The duct vent 108 can include one or more feature that allow the air flow to be regulated. For example, the duct vent 108 can include a switch that controls the amount of air that can pass through the duct vent 108. The duct vent 108 can include a filtration system such as the filtration system disclosed in Non-Provisional patent application Ser. No. 14/097,142 incorporated herein by reference in its entirety.

FIG. 1 additionally shows that the HVAC fluid dispersant system 100 can include one or more fluid lines 110. The fluid line 110 allow fluid to be moved throughout the HVAC system. For example, the rigid or flexible fluid line 110 can be affixed mounted, placed and/or un-affixed or loosely positioned along the duct system 106, either internally or externally or some combination thereof, to ensure that the fluid can be moved to any location serviced by the duct system 106. The fluid line 110 can be a high pressure fluid line. The fluid line 110 can be made of any desired material, such as reinforced nylon tubing or metals such as copper or stainless steel. As used in the specification and the claims, the phrase "configured to" denotes an actual state of configuration that fundamentally ties recited elements to the physical characteristics of the recited structure. That is, the phrase "configured to" denotes that the element is structurally capable of performing the cited element but need not necessarily be doing so at any given time. As a result, the phrase "configured to" reaches well beyond merely describing functional language or intended use since the phrase actively recites an actual state of configuration.

FIG. 1 moreover shows that the HVAC fluid dispersant system 100 can include a pump 112. A pump 112 is a device that moves fluids (liquids or gases), or sometimes slurries, by mechanical action. The pump 112 operates by some mechanism (typically reciprocating or rotary), and consumes energy to perform the mechanical work of moving fluid. The pump 112 can include any pump that is capable of moving fluid through the fluid line 110. For example, the pump 112 can include a high pressure compressor pump.

FIG. 1 also shows that the HVAC fluid dispersant system 100 can include a filter 114. The filter 114 removes impurities from the fluid by means of a fine physical barrier, a chemical process or a biological process. That is, the filter 114 includes a device (e.g., a membrane or layer) that is designed to physically block certain objects or substances while letting the majority of the fluid pass through. Thus, the fluid that is dispersed can be free of, or have a reduced amount of, impurities that may damage the HVAC system or cause other problems.

FIG. 1 further shows that the HVAC fluid dispersant system 100 can include a source line 116. The source line 116 delivers the fluid to the pump 112 to be moved through the fluid line 110. For example, the source line 116 can include a water line connected to a water line within a building. The source line 116 can pass through the filter 114 before the fluid is passed to the pump 112 or the source pump 112 can receive the fluid from the source line 116 then pass the fluid through the filter 114.

FIG. 1 further shows that the HVAC fluid dispersant system 100 can include a point of entry 118. The point of entry 118 is a location where the fluid line 110 pass from the exterior of the duct system 106 to the interior of the duct system 106. The point of entry 118 may be created to accommodate the fluid line 110 or can be a preexisting opening, such as a seam in a duct or joint, that allows for insertion of the fluid line 110. One of skill in the art will appreciate that if the fluid line 110 are exterior to the duct system 108 then a point of entry 118 is unneeded. Likewise, if only a portion of the fluid line 110 are exterior to the duct system 108 then more than a single point of entry 118 may be required.

FIG. 1 additionally shows that the HVAC fluid dispersant system 100 can include one or more fluid line connectors 120. The fluid line connectors 120 allow for the interconnections among the fluid line 110. Additionally or alternatively, the fluid line connectors 120 can allow the fluid line 110 to change direction. For example, the fluid line connectors 120 can include an elbow (which allows for a 90-degree change of direction), a t-connector (which allows a single input to be divided into two outputs or vice versa), an x-connector (which allows a single input to be divided into three outputs) or any other desired connector.

FIG. 1 moreover shows that the HVAC fluid dispersant system 100 can include a switch 122. The switch 122 can be used to allow or prevent flow of electricity to the components of the HVAC fluid dispersant system 100. The switch 122 is an electrical component that can break an electrical circuit, interrupting the current or diverting it from one conductor to another. The mechanism of a switch may be operated directly by a human operator to control a circuit (for example, a light switch or a keyboard button), may be operated by a moving object such as a door-operated switch, may be operated by some sensing element for pressure, temperature or flow or any combination thereof.

FIG. 1 also shows that the HVAC fluid dispersant system 100 can include a control system 124. The control system 124 is a device, or set of devices, that manages, commands, directs or regulates the behavior of other devices or systems within the HVAC fluid dispersant system 100. For example, the control system 124 can provide power to the pump 112 when the HVAC fluid dispersant system 100 is active. The control system 124 can operate the pump 112 or other elements of the HVAC fluid dispersant system 100 when a set of conditions are met. For example, the control system 124 can follow a schedule, can turn on the HVAC fluid dispersant system 100 when the blower is active, can be operated only when the humidity is below —or above—a certain level (e.g., a humidistat can be connected for sensing humidity levels), or can operate under any other desired set of conditions. One of skill in the art will appreciate that a single control can allow for distribution of multiple fluids. For example, the HVAC fluid dispersant system 100 can include a second set of fluid line 110, a second pump 112, a second source line 116, etc. that allows for additional fluid dispersal. For example, the first fluid can be water to increase humidity and the second fluid can include a scented fluid. The first fluid and the second fluid need not be distributed according to the same set of conditions. That is, the first fluid can be distributed by the control system 124 according to a first set of conditions and the second fluid can be distributed by the control system 124 according to a second set of conditions.

FIG. 1 further shows that the HVAC fluid dispersant system 100 can include a power source 126. The power source 126 includes any mechanism for supplying electrical power to the HVAC fluid dispersant system 100. For example, the power source 126 can include a plug. I.e., the power source 126 can be plugged into an outlet.

FIG. 1 also shows that the HVAC fluid dispersant system 100 can include a mist 128. As the pump 112 pumps the fluid through the fluid line 110 the fluid is passed through a nozzle that creates a mist 128 near the duct vent 108. When the blower 104 is moving air through the duct system 106 then the air exiting the duct vent 108 will disperse the mist 128 due to the air flow.

Figure 2:
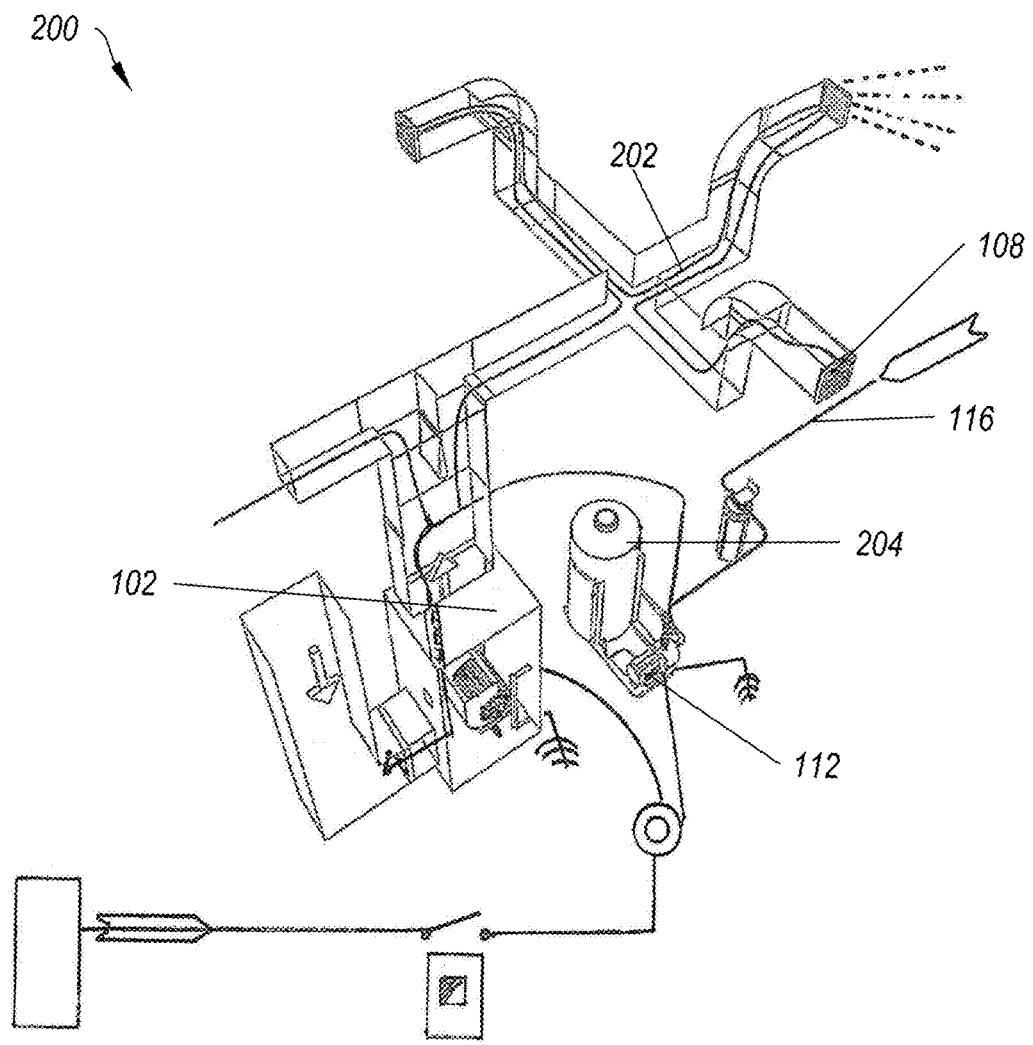
FIG. 2 illustrates an alternative example of a HVAC fluid dispersant system.

FIG. 2 illustrates an alternative example of a HVAC fluid dispersant system 200. The HVAC fluid dispersant system 200 disperses the fluid both at the intake of the air handler 102 and at the duct vent 108. The fluid dispersal at the intake is described below. Likewise, the HVAC fluid dispersant system 200 does not require fluid line connectors. I.e., the fluid travels through only a single fluid line 202.

FIG. 2 shows that the HVAC fluid dispersant system 200 can include a fluid tank 204. The fluid tank 204 allows for storage of the fluid and accumulation of the fluid when the HVAC fluid dispersant system 200 is not in use. For example, if the flow rate of the fluid from the source line 116 is below the flow rate of the fluid through the pump 112 and fluid line 202 then the fluid tank 204 can be used to provide the extra needed fluid while the pump 112 is operating.

Figure 3A:
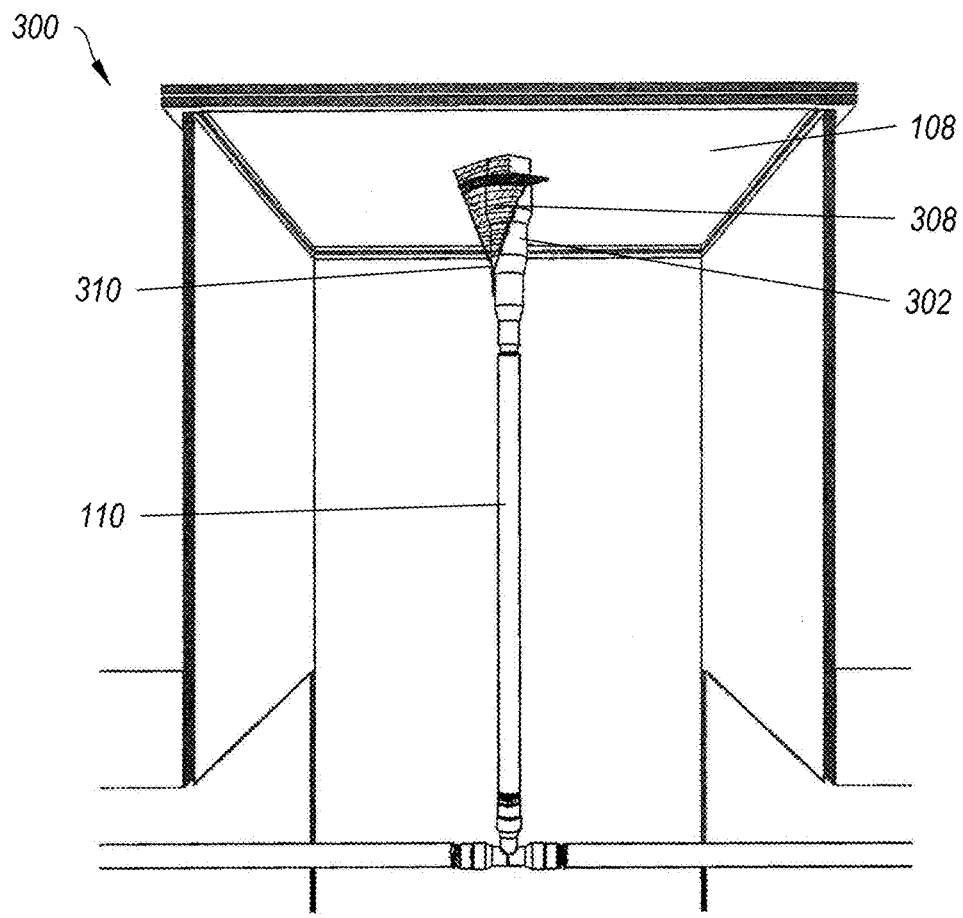
FIG. 3A illustrates a rear (or duct side) perspective view of the example of a misting system.
Figure 3B:
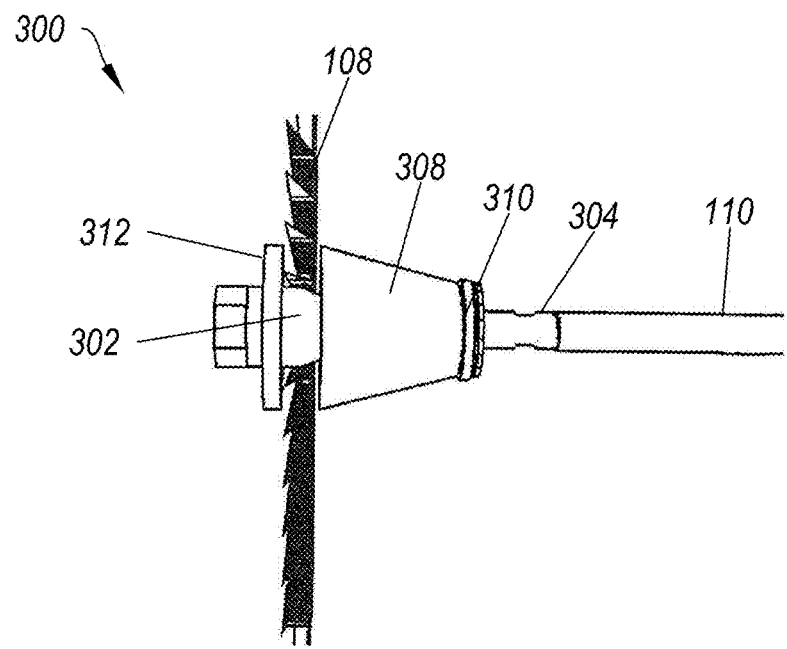
FIG. 3B illustrates a side view of the example of a misting system.
Figure 3C:
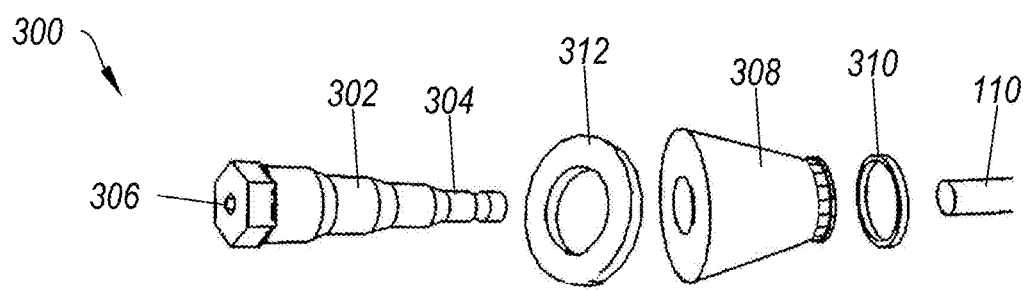
FIG. 3C illustrates an exploded view of the example of a misting system.

FIGS. 3A, 3B and 3C (collectively "FIG. 3") illustrate an example of a misting system 300. FIG. 3A illustrates a rear (or duct side) perspective view of the example of a misting system 300; FIG. 3B illustrates a side view of the example of a misting system 300; and FIG. 3C illustrates an exploded view of the example of a misting system 300. The misting system 300 produces a mist at the duct vent 108. I.e., the misting system 300 produces a mist that will exit the HVAC system to produce the desired result in the area treated by the HVAC system.

FIG. 3 shows that the misting system 300 can include a misting nozzle 302. The misting nozzle 302 receives fluid from the fluid line 110 and creates a mist composed of the fluid. I.e., the nozzle 302 is a device designed to control the direction or characteristics of the fluid flow (especially to increase velocity) as it exits the fluid line 110. The nozzle 302 can include a pipe or tube of varying cross sectional area, and it can be used to direct or modify the flow of the fluid (liquid or gas). The nozzle 302 can used to control the rate of flow, speed, direction, mass, shape, and/or the pressure of the stream that emerges from the fluid line 110. In particular, the nozzle 302 increase the velocity of the fluid at the expense of the fluid's pressure energy. One of skill in the art will appreciate that the nozzle 302 can be attached to the duct vent 108 or can be within the duct system 106. I.e., the mist created by the nozzle 102 can be created within the duct system 106, external to the duct system 106, or partially within the duct system 106 and partially external to the duct system 106.

FIG. 3 also shows that the misting system 300 can include a nozzle connector 304. The nozzle connector 304 connects the nozzle 302 to the fluid line 110. That is, the nozzle connector 304 allows fluid to pass from the fluid line 110 into the nozzle 302.

FIG. 3 further shows that the misting system 300 can include an aperture 306. The aperture 306 is the point or opening at which the fluid exits the nozzle 302. The size and shape of the aperture 306 can change the spray pattern produced by the nozzle 302. For example, the aperture 306 as a slot can create a wide flat spray and a small hole as the aperture 306 can produce a jet of fluid.

FIG. 3 additionally shows that the misting system 300 can include a rear anchor 308. The rear anchor 308 fixes the nozzle 302 relative to the duct vent 108. I.e., the rear anchor 308 ensures that that the nozzle 302, or at least a portion thereof, does not move relative to the duct vent 108. For example, the rear anchor 308 can include a flange or other device that secures the nozzle 302. In particular, the flange of the rear anchor 308 can prevent the nozzle from pushing out through the duct vent 108.

FIG. 3 moreover shows that the misting system 300 can include a fastening band 310. The fastening band 310 secures the nozzle 302 to the rear anchor 308. That is the fastening band 310 provides a force, either through elastic tension or mechanical tightening, that secures the nozzle 302 to the rear anchor 308.

FIG. 3 also shows that the misting system 300 can include a front collar 312. The front collar 312 prevents the nozzle 302 from being pushing into the duct vent 108. I.e., the front collar ensures that a portion of the nozzle 302, especially the aperture 306, remains outside of the duct vent 108.

Figure 4A:
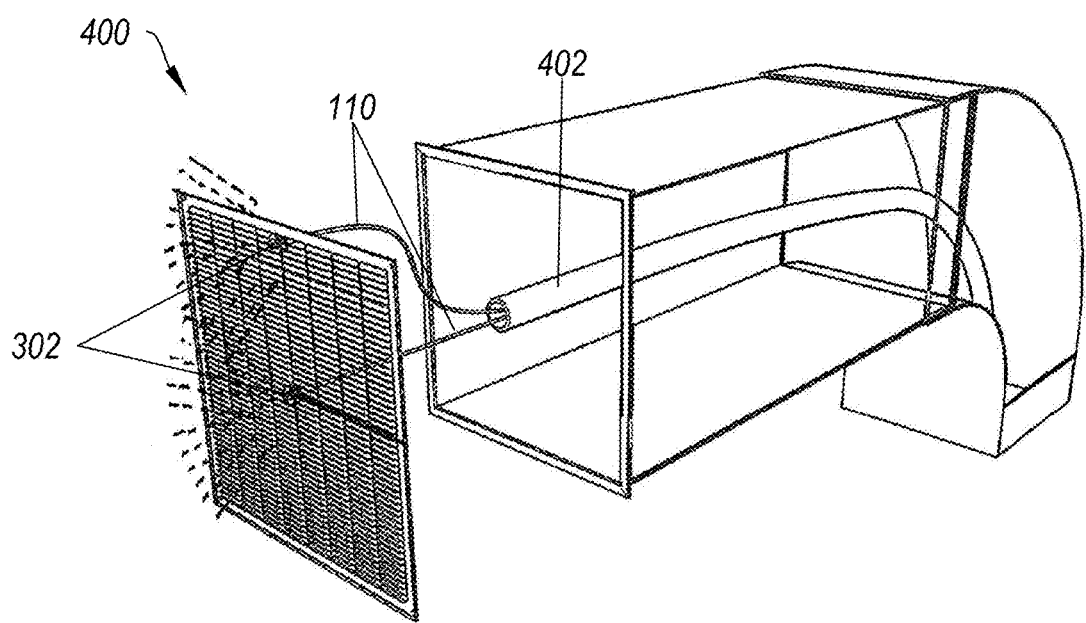
FIG. 4A illustrates a front perspective exploded view of the example of an alternative misting system.
Figure 4B:
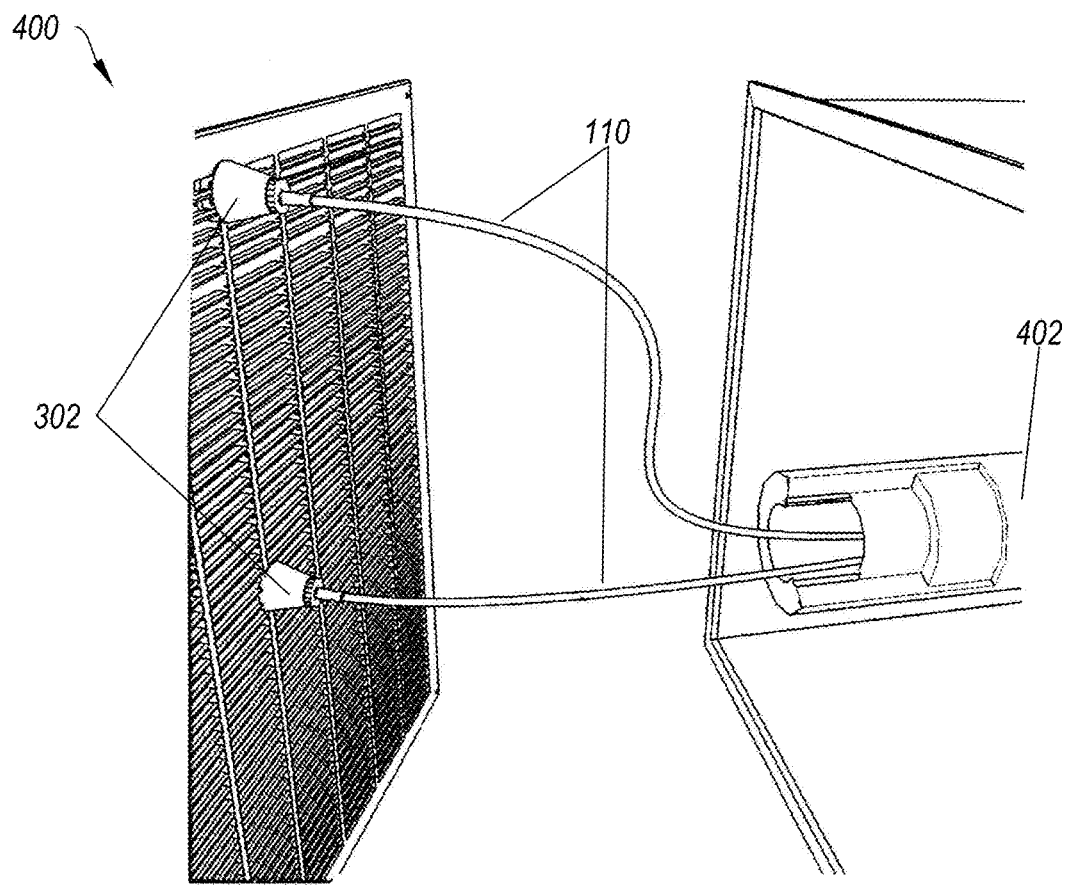
FIG. 4B illustrates a rear perspective exploded view of the example of an alternative misting system.

FIGS. 4A and 4B (collectively "FIG. 4") illustrate an example of an alternative misting system 400. FIG. 4A illustrates a front perspective exploded view of the example of an alternative misting system 400; and FIG. 4B illustrates a rear perspective exploded view of the example of an alternative misting system 400. The misting system 400 allows for multiple fluids to be used in creating a mist. The fluids can be used simultaneously or can be used at different times relative to one another. For example, the first fluid could include water to increase humidity and the second fluid can include an antimicrobial agent.

FIG. 4 shows that the misting system 400 can include fluid line insulation 402. The fluid line insulation 402 can be used to ensure that the multiple fluid lines 110 remain in place relative to one another. That is, the fist fluid line 110 and the second fluid line 110 are both enclosed in fluid line insulation 402 so both can be installed together. The fluid line insulation 402 can then be removed near the nozzles 302 so that the fluid lines can be routed to the nozzles 302. Additionally or alternatively, the fluid line insulation 402 can ensure that condensation does not form which could, over time, compromise the HVAC system.

Figure 5:
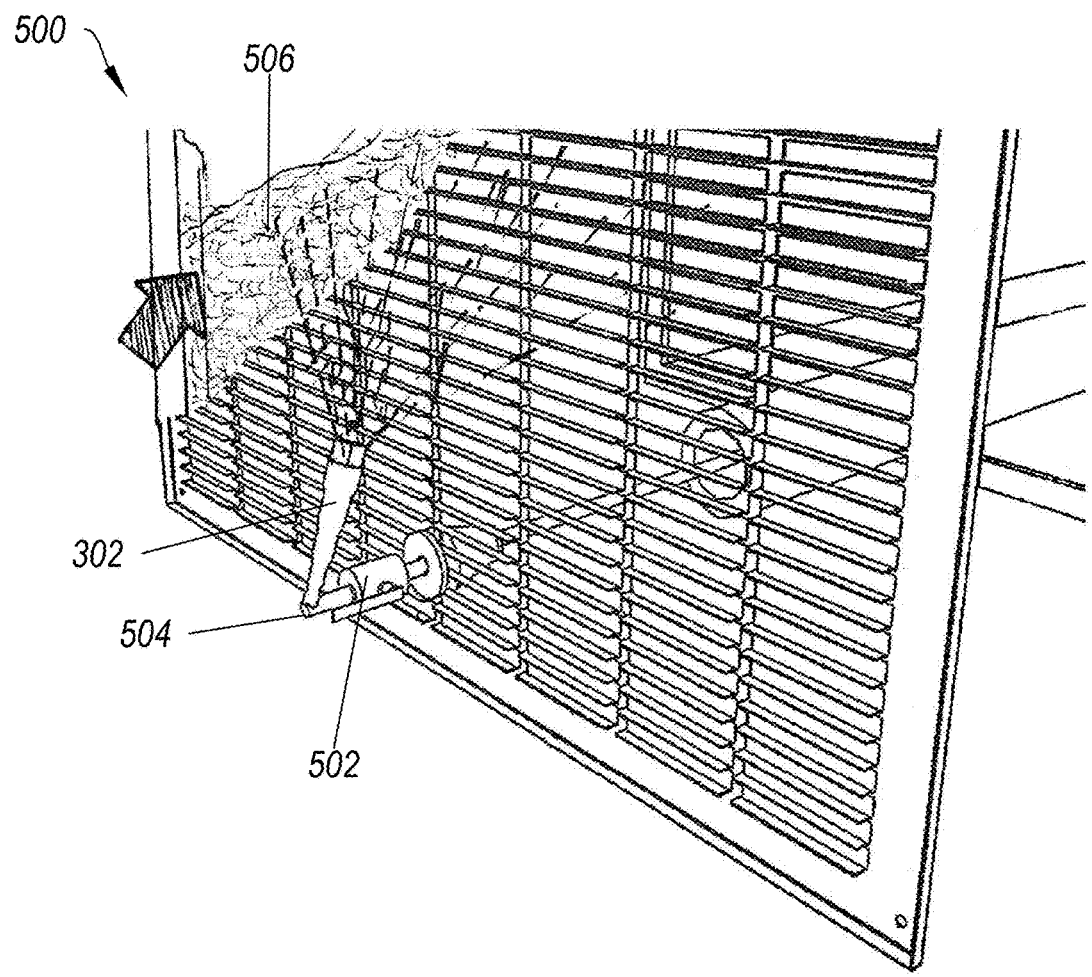
FIG. 5 illustrates an example of an air return misting system.

FIG. 5 illustrates an example of an air return misting system 500. The air return is the location where air is provided to the HVAC system. The air return can include either from the interior of the space serviced by the HVAC system or external to the space. I.e., the air return can obtain outside air to provide to the HVAC system to can recirculate air from the interior of the space serviced by the HVAC system.

FIG. 5 shows that the air return misting system 500 can include a valve 502. A user may wish for the air return misting system 500 to be operational only at certain times or during certain conditions; therefore, the valve 502 can allow for the air return misting system 500 to be turned off manually. I.e., the valve 502 can be closed if a user desires the air return misting system 500 to be turned off and can be opened if a user desires the air return misting system 500 to the turned on.

FIG. 5 also shows that the air return misting system 500 can include re-directional hardware 504. Re-directional hardware 504 allows the direction of the spray from the nozzle 302 to be changed. For example, the spray may be directed such that the mist is parallel to the air return. This can allow the mist to be evenly coat a portion of the return air filter 506.

Figure 6:
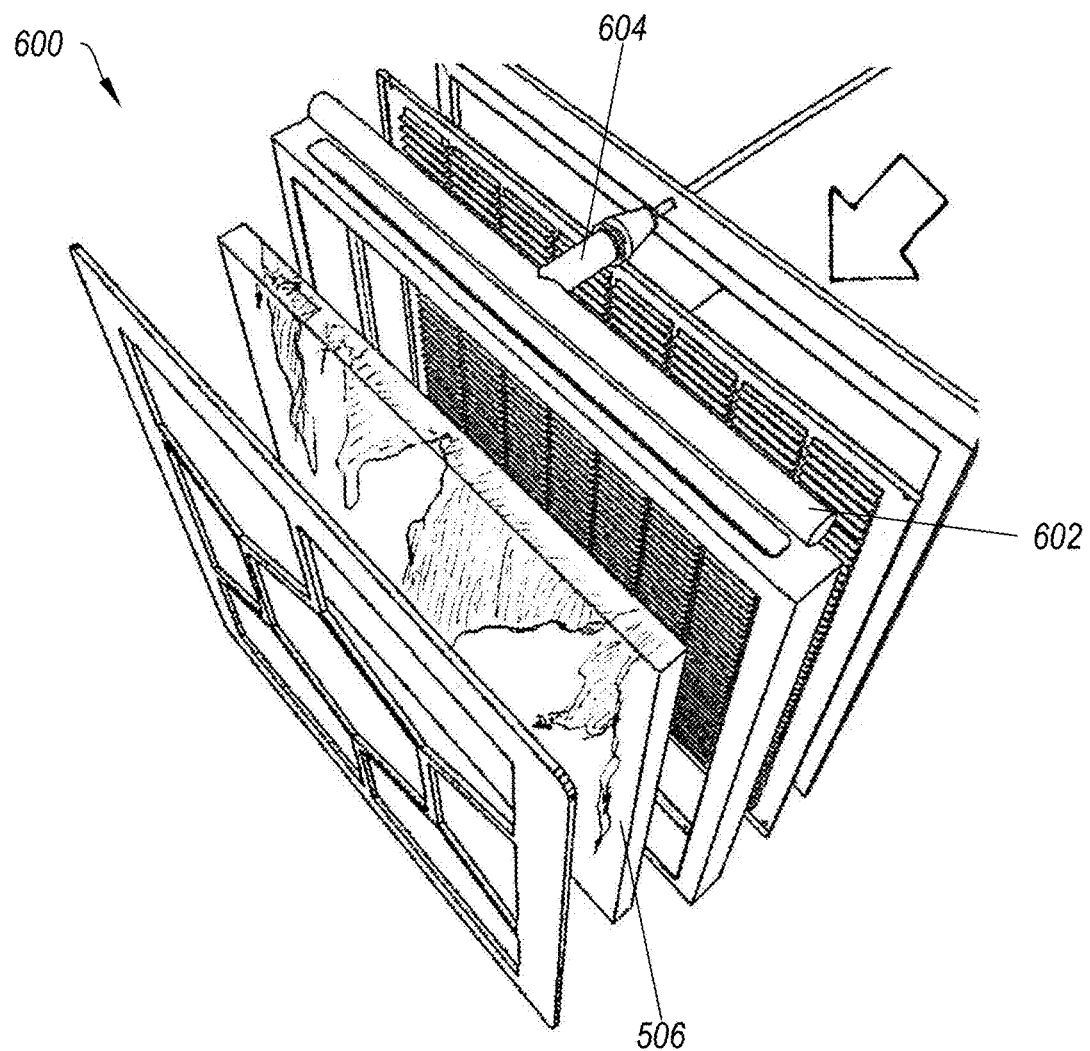
FIG. 6 illustrates an example of air return drip system.

FIG. 6 illustrates an example of air return drip system 600. The air return drip system adds the fluid to the return air filter 506. That is, rather than producing a mist the drip system can include an aftermarket air filter 506 such as the filtration system disclosed in Non-Provisional patent application Ser, No. 14/097,142 previously incorporated.

FIG. 6 shows that the air return drip system 600 can include a drip nozzle 602. The drip nozzle 602 extrudes the fluid either a drop at a time or as a stream. This, the fluid is applied directly to the air filter 506 in the return air filter 506. The drip nozzle 602 can include multiple outlets such that the fluid is placed on the filter at multiple locations.

FIG. 6 also shows that the air return drip system 600 can include a drip nozzle connector 604. The drip nozzle connector 604 connects the drip nozzle 602 to the fluid line 110. I.e., the drip nozzle connector 604 allows fluid to pass from the fluid line 110 into the drip nozzle 602.

Figure 7:
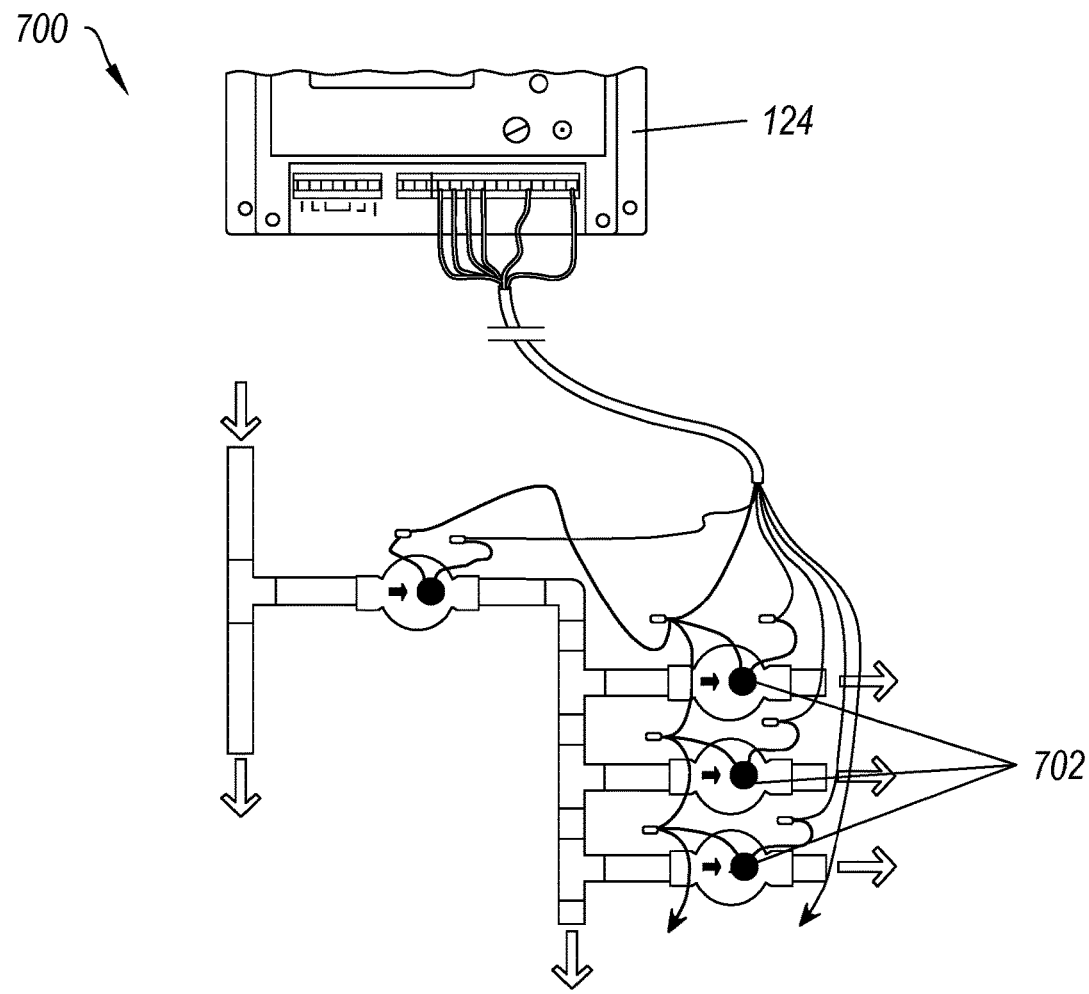
FIG. 7 illustrates an example of a manifold.

FIG. 7 illustrates an example of a manifold 700. A manifold is an intake channel, the flow frim which is directed into one or more exit channels. The manifold 700 allows for only certain portions of the HVAC fluid dispersant system to be used. For example, a first portion can be used for humidification of a certain floor, antimicrobial solution to be misted into a particular room and air freshener to be distributed to the whole space covered by the HVAC system. The manifold 700 is connected to the control system 124.

FIG. 7 shows that the manifold 700 can include one or more solenoid valves 702. The solenoid valve 702 is an electromechanically operated valve. The solenoid valve 702 is controlled by an electric current through a solenoid: in the case of a two-port valve the flow is switched on or off; in the case of a three-port valve, the outflow is switched between the two outlet ports. Solenoids offer fast and safe switching, high reliability, long service life, good medium compatibility of the materials used, low control power and compact design.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An HVAC fluid dispersant system, the HVAC fluid dispersant system comprising:
   one or more fluid lines, the one or more fluid lines configured to allow movement of a fluid;
   a pump, the pump configured to move the fluid through the one or more fluid lines;
   a source line, the source line configured to provide the fluid to the pump;
   a nozzle, wherein the nozzle is configured to:
      receive the fluid from the one or more fluid lines;
      create a mist composed of the fluid; and
      attach to a duct vent; and
   an air return misting system, wherein the air return misting system includes:
      a drip nozzle, the drip nozzle dripping fluid on a return air filter.

2. The HVAC fluid dispersant system of claim 1, further comprising:
   a fluid filter, the fluid filter configured to remove impurities from the fluid.

3. The HVAC fluid dispersant system of claim 1, further comprising:
   a fluid line connector, the fluid line connector connecting two or more fluid lines.

4. The HVAC fluid dispersant system of claim 1, wherein the fluid includes:
　water.

5. The HVAC fluid dispersant system of claim 1, wherein the fluid includes:
　an antimicrobial solution.

6. The HVAC fluid dispersant system of claim 1, wherein the fluid includes:
　an air freshening fluid.

7. The HVAC fluid dispersant system of claim 1, wherein the fluid includes:
　an aromatherapy fluid.

8. The HVAC fluid dispersant system of claim 1, wherein:
　at least a portion of the one or more fluid lines are located within a duct system of an HVAC system.

9. The HVAC fluid dispersant system of claim 1, wherein:
　at least a portion of the one or more fluid lines are attached to the exterior of a duct system of an HVAC system.

10. An HVAC fluid dispersant system, the HVAC fluid dispersant system comprising:
　one or more fluid lines, the one or more fluid lines configured to allow movement of a fluid;
　fluid line insulation;
　a pump, the pump configured to move the fluid through the one or more fluid lines;
　a source line, the source line configured to provide the fluid to the pump;
　a nozzle, wherein the nozzle is configured to:
　　receive the fluid from the one or more fluid lines;
　　create a mist composed of the fluid; and
　　attach to a duct vent;
　a control system wherein the control system is configured to control operation of the system based on a set of conditions; and
　an air return misting system, wherein the air return misting system includes:
　　a drip nozzle, the drip nozzle dripping fluid on a return air filter.

11. The HVAC fluid dispersant system of claim 10, wherein the set of conditions includes a timer.

12. The HVAC fluid dispersant system of claim 10, wherein the set of conditions includes a humidity measurement.

13. The HVAC fluid dispersant system of claim 10, wherein the set of conditions includes when the blower fan of the HVAC system is turned on.

14. An HVAC fluid dispersant system, the HVAC fluid dispersant system comprising:
　one or more fluid lines, the one or more fluid lines carrying a fluid;
　fluid line insulation;
　a pump, the pump moving the fluid through the one or more fluid lines;
　a source line, the source line providing the fluid to the pump;
　a nozzle, wherein the nozzle:
　　receives fluid from the one or more fluid lines;
　　creates a mist composed of the fluid; and
　　attaches to a duct vent;
　　includes an aperture, the aperture allowing the mist to exit the nozzle;
　a rear anchor, the rear anchor preventing the nozzle from extending beyond the duct vent more than a predetermined amount;
　a fastening band, the fastening band securing the rear anchor to the nozzle;
　a front collar the front collar preventing the nozzle from retracting into the duct vent more than a predetermined amount;
　a control system wherein the control system controls operation of the system based on a set of conditions; and
　an air return misting system, wherein the air return misting system includes:
　　a drip nozzle, the drip nozzle dripping fluid on a return air filter.

15. The HVAC fluid dispersant system of claim 14 wherein the air return misting system includes:
　a nozzle, the nozzle dispersing fluid as a mist near the air return vent.

16. The HVAC fluid dispersant system of claim 14 wherein the air return misting system includes:
　a valve, the valve allowing a user to turn on and off the air return misting system.

17. The HVAC fluid dispersant system of claim 14 wherein the air return misting system includes:
　re-directional hardware, the re-directional hardware allowing a user to control the direction of the fluid output.

18. The HVAC fluid dispersant system of claim 14 further comprising:
　a manifold, the manifold allows for certain portions of the HVAC fluid dispersant system to be used independent of one another.

\* \* \* \* \*